US00PP27871P3

(12) United States Plant Patent
Stokes et al.

(10) Patent No.: US PP27,871 P3
(45) Date of Patent: Apr. 11, 2017

(54) BLACK RASPBERRY PLANT NAMED 'OHIO'S TREASURE'

(50) Latin Name: ***Rubus occidentcelis* L.**
Varietal Denomination: Ohio's Treasure

(71) Applicants: Benjamin Dale Stokes, Wilmington, OH (US); Harry Jan Swartz, Oakland, MD (US)

(72) Inventors: Benjamin Dale Stokes, Wilmington, OH (US); Harry Jan Swartz, Oakland, MD (US)

( * ) Notice: Subject to any disclaimer, the term of this patent is extended or adjusted under 35 U.S.C. 154(b) by 65 days.

(21) Appl. No.: 14/545,378

(22) Filed: Apr. 28, 2015

(65) Prior Publication Data

US 2016/0324046 P1 Nov. 3, 2016

(51) Int. Cl.
*A01H 5/08* (2006.01)

(52) U.S. Cl.
USPC ..... Plt./204

(58) Field of Classification Search
USPC ..... Plt./203, 204
See application file for complete search history.

*Primary Examiner* — Susan McCormick Ewoldt
(74) *Attorney, Agent, or Firm* — Flynn, Thiel, Boutell & Tanis, P.C.

(57) ABSTRACT

A new and distinct cultivar of primocane and floricane fruiting black raspberry plant 'Ohio's Treasure'. The new cultivar fruits from normal overwintered floricane buds, on primocanes, and from late spring, long, basal, floricane trusses which result in good productivity over a particularly long harvest season.

6 Drawing Sheets

BACKGROUND OF THE INVENTION

The present invention relates to a new and distinct cultivar of primocane and floricane fruiting black raspberry variety. The new cultivar is distinguished from other black raspberry cultivars by its ability to fruit on primocanes and late spring, long, basal, floricane trusses, which result in good productivity over a particularly long harvest season. 'Ohio's Treasure' fruit is not firm enough to ship, therefore, 'Ohio's Treasure' is suitable to extend the black raspberry season for homeowners and local marketing channels.

DESCRIPTION OF RELATED PRIOR ART

Several wild selections of primocane fruiting (commonly known as "fall bearing") black raspberry have been found and named, including 'Ohio Everbearing' (unpatented). These are unimproved and generally reported to be small fruited and low yielding. 'Black Knight' black raspberry (unpatented), has been named and is useful in extending the season by producing late spring or early summer fruit on long basal trusses which ripen later. As these canes arise from the base of the floricane and do not extend the season into the fall, 'Black Knight' is not truly a primocane fruiting black raspberry. Only one other improved cultivar of fall fruiting black raspberry is known, 'Explorer' (U.S. Plant Pat. No. 17,727).

The new and distinct cultivar of the present invention is a raspberry plant named 'Ohio's Treasure'. Both 'Ohio's Treasure' and 'Explorer' produce fruit from true primocanes in the fall, unlike 'Black Knight'. 'Ohio's Treasure' differs from 'Explorer' in that 'Ohio's Treasure' fruit also arise from large basal floricane fruiting trusses, such as occurs on 'Black Knight'. 'Explorer' is the result of hybridizing wild black raspberries with primocane fruiting habits. Like its wild progenitors, 'Explorer' fruit is relatively small compared to some commercial floricane fruiting cultivars such as 'Jewel' (unpatented) and 'Dundee' (unpatented). 'Ohio's Treasure' is the result of crossing relatively larger fall bearing red raspberries with black raspberry characteristics, round fruit with dark color, with black raspberry cultivars with a tendency to produce large basal floricane trusses. Selfed seed from 'Ohio's Treasure' may therefore produce purple-black fruit, unlike 'Explorer' selfed seed which should only produce black fruited seedlings. As there have been informal reports of self sterility in 'Explorer' plants, eliminating the possibility of selfed seed, crosses of 'Explorer' with other black raspberry cultivars should only produce black raspberry seedlings.

SUMMARY OF THE CULTIVAR

The following is a summary of a new and distinct black fruited, primocane and floricane fruiting, raspberry cultivar, botanically known as *Rubus occidentalis* L. The following characteristics are outstanding:

1. Production of black raspberry fruit sequentially from normal floricane trusses, then longer, later spring, basal floricane trusses, and finally unpruned and then pruned primocanes. This produced an extended season of harvest, from June 27 to October 11 in pot culture in tunnels, with only a two week cropping hiatus in early August.
2. Compared to the only other patented primocane fruiting black raspberry cultivar, 'Ohio's Treasure' fruit is over 25% heavier.
3. 'Ohio's Treasure' canes are more productive than the other fall fruiting black raspberry, producing 2.05 lbs of fruit per plant, similar to the leading commercial cultivar, 'Jewel', which only produces fruit on floricanes.
4. 'Ohio's Treasure' fruit is black and has the fruit shape, aroma and flavor of black raspberries. 'Ohio's Treasure' fruit is relatively soft, but it separates from its receptacle early and completely, allowing unripe fruit picking and extra days of storage, some transport and the possibility of mechanical harvest for processing.

These characteristics make 'Ohio's Treasure' suitable as a summer and fall fruiting variety for direct or farm marketed fruit growers and homeowners. 'Ohio's Treasure' fruit are considered too small and soft for long term storage or commercial fresh market shipping. In cooler areas with less than 2500 growing degree days (base 50° F.), 'Ohio's Treasure' primocane fruit ripens in mid-August and, with mid-summer topping, through September, making it sufficiently early to use as a primocane bearer for almost all agricultural regions in the United States. Although the chill requirement for 'Ohio's Treasure' was not directly measured, all other black raspberries have chill hour requirements over 1200 hours. Therefore, no recommendation is made for the adaptation of 'Ohio's Treasure' in low chilling areas. Some fall bearing red raspberries are used commercially in low chill areas as they do not need to have chilled floricanes to produce a crop. Floricanes of 'Ohio's Treasure' have survived exposure of −16 F (−27 C) while dormant.

ORIGIN OF THE NEW CULTIVAR

The new cultivar of fall bearing black raspberry originated from a controlled cross performed at Oakland, Md. The cross, designated: "AL", was 'Dundee', female parent (unpatented)×XEF-o1, male parent (unpatented) and was made in the winter of 2006. 'Dundee' is a floricane fruiting black raspberry selection with several interesting fruit quality attributes, including fruit size and reasonable fruit firmness. It also has a tendency to produce basal flower buds which produce long flower trusses on the basal 5 inches of a floricane. These trusses produce larger fruit later than the more apical, and shorter, floricane trusses. These basal trusses are different from true primocane fruiting laterals or canes in season of harvest and fruit size. XEF-o1 is a floricane and primocane fruiting purple fruited cultivar from a black raspberry×red raspberry cross with several desirable fruit attributes: dark color and round fruit similar to black raspberries, fruit weight of over 3 grams in Ohio, and very high yields, especially on primocanes. The cross was made to produce a round fruited primocane bearing black raspberry type to further extend the black raspberry harvest season with two additional fruiting seasons.

XEF-o1 is a cross of TAN-u1black raspberry selection (unpatented) made in Upper Marlboro, Md. and 'Josephine' (U.S. Plant Pat. No. 12,173). TAN-u1 is a cross of 'Jewel' black raspberry (unpatented)×PAO-f1 (unpatented), a dark fruited fall bearing raspberry selection made in Cream Ridge, N.J. Like 'Dundee', its progeny, 'Jewel' also produces long basal floricane trusses with large fruit. PAO-f1 contains the dark fruited 'Caroline' (U.S. Plant Pat. No. 10,412) and round fruited 'Southland' (unpatented) fall bearing red raspberries.

The year of crossing was designated "A" as part of a certified breeding program in Oakland, Md. The seed from this cross was germinated and grown to transplant size. The seedlings were transported to a raspberry farm outside of Wilmington, Ohio and planted in the field in May, 2007. The present invention was third seedling of the "AAL" progeny selected in August, 2008 and was therefore designated "-o3". Thus, the complete breeding designation of 'Ohio's Treasure' is "AAL-o3".

ASEXUAL PROPAGATION OF THE VARIETY

'Ohio's Treasure' has been asexually propagated by tissue culture in Oakland, Md. and by rooted vegetative primocane nodes from 2010 to present. No off-type plants have been observed in the history of asexual propagation of this cultivar by either method and fall bearing characteristics occurs normally on propagated plants. Tissue culture shoots readily establish in culture and branching is easier to stimulate than with other black raspberry cultivars.

BRIEF DESCRIPTION OF THE DRAWINGS

The accompanying photographs show typical characteristics of the new variety, all color plate references are from The Royal Horticultural Society ("R.H.S."), London, UK SW1P 2PE, 4$^{th}$ edition, 2001, Colour Plates.

Figure 1:
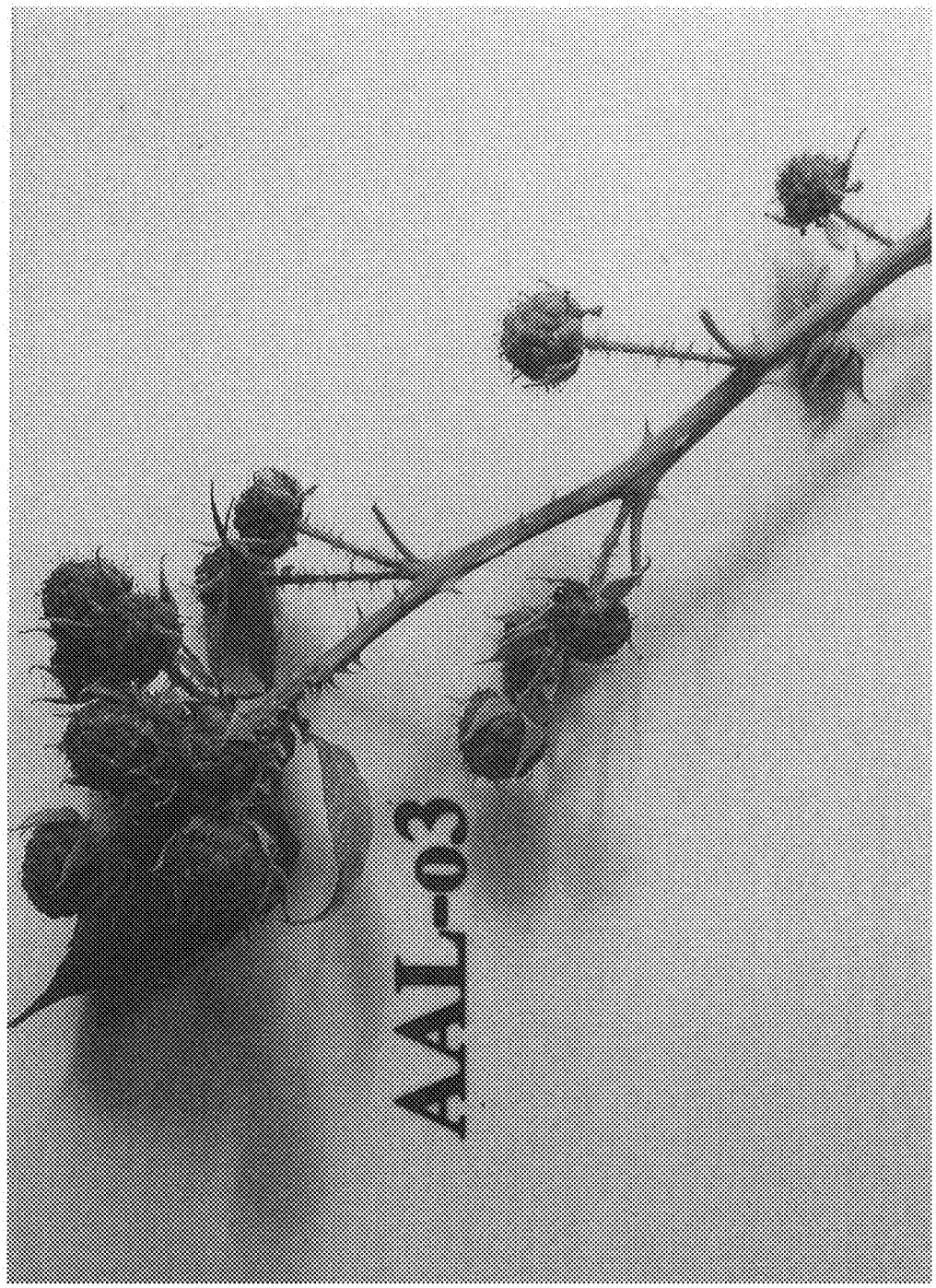
FIG. 1. shows a long floricane truss which arose from a basal bud of 'Ohio's Treasure' with leaves removed to show the distribution of immature fruit, cane waxiness, and the color, size and pattern of thorns during the growing season.

Colors in the drawings are only approximated, in cases where the colors in the drawings differ from the R.H.S. color designation given herein, the R.H.S. designation should be considered the most accurate.

DESCRIPTION OF THE NEW CULTIVAR

The following is a detailed description of 'Ohio's Treasure', including fruit production, together with the cultivar's morphological characteristics. 'Ohio's Treasure' is a species hybrid, which contains a predominance of *Rubus occidentalis* L. genetic background and traits and would be botanically classified in that species commonly referred to as black raspberries. The description is based on information from plants grown in the greenhouses at Oakland, Md. or the breeding field in Wilmington, Ohio.

Cane Types Based on Floral Pattern: 'Ohio's Treasure' produces only crown suckers (=canes or shoots) and average 8.5 new canes per plant in the second year and beyond. During the growing season, all trusses and canes are light green colored (RHS Colour Plate No. 191C). Canes have a strong waxy coating (FIGS. 1, 2 and 3) which is easily removed with finger contact. Depending on plant vigor, half of the canes branch the first year after planting and are semi-erect and readily branch by the second year of a plant's growth. In the second year, four types of canes are observed.

1. For a vegetative cane which terminates in a "rat tail" suitable for tip layering (FIG. 2), total node number per cane averages 89 for second year plants; cane length averages 265 cm. Two spines on average occur on each midcane node, or 20 spines per 30 cm. Spines are more numerous and reduced in size on the apical rat tail section of vegetative canes. Each cane produce mid cane branches 5 times on average. No fruit are produced on these primocanes during the first year.

Figure 2:
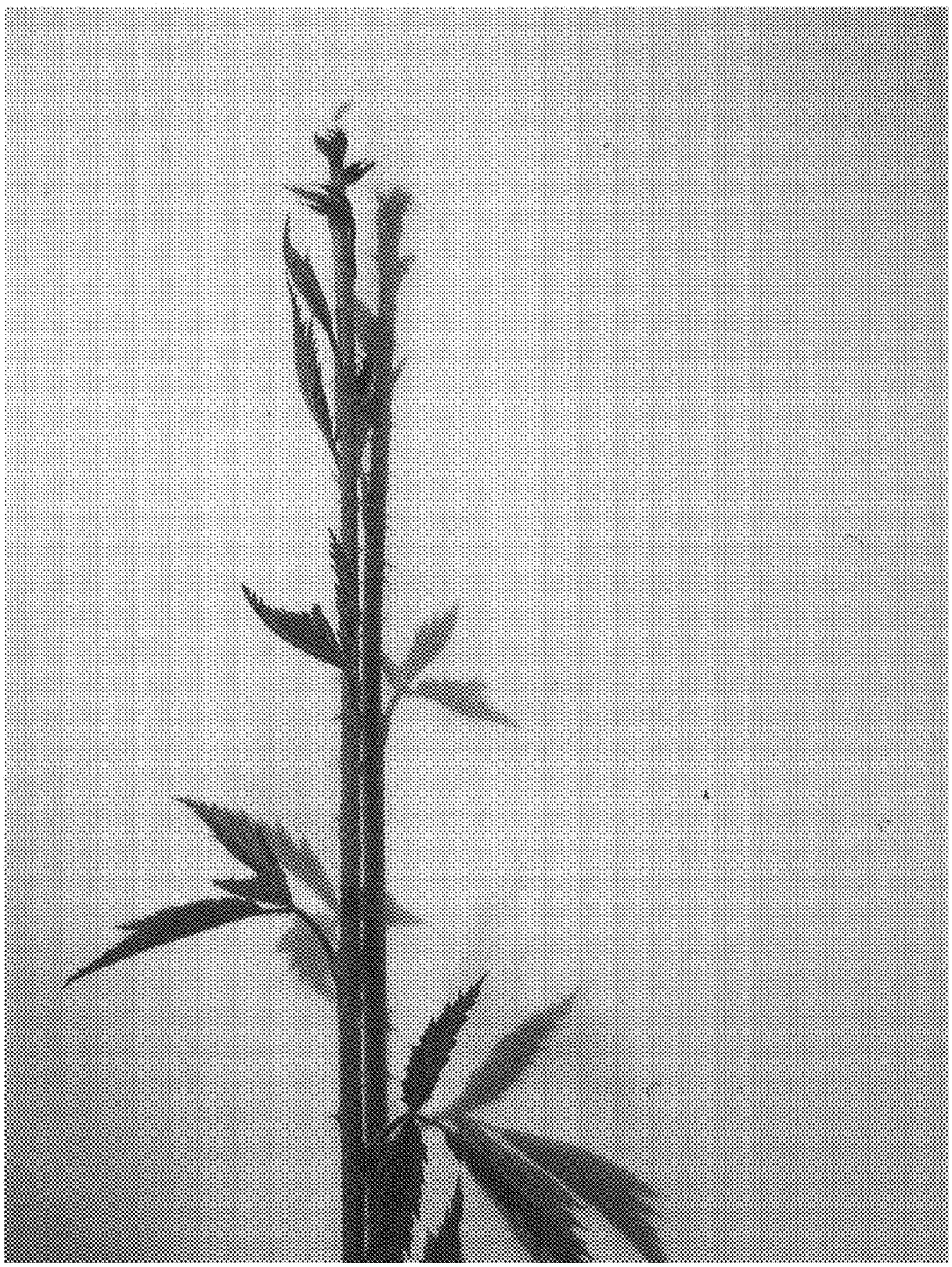
FIG. 2. shows a vegetative "rat tail" cane tip with its more needle-like thorns in October.
Figure 3:
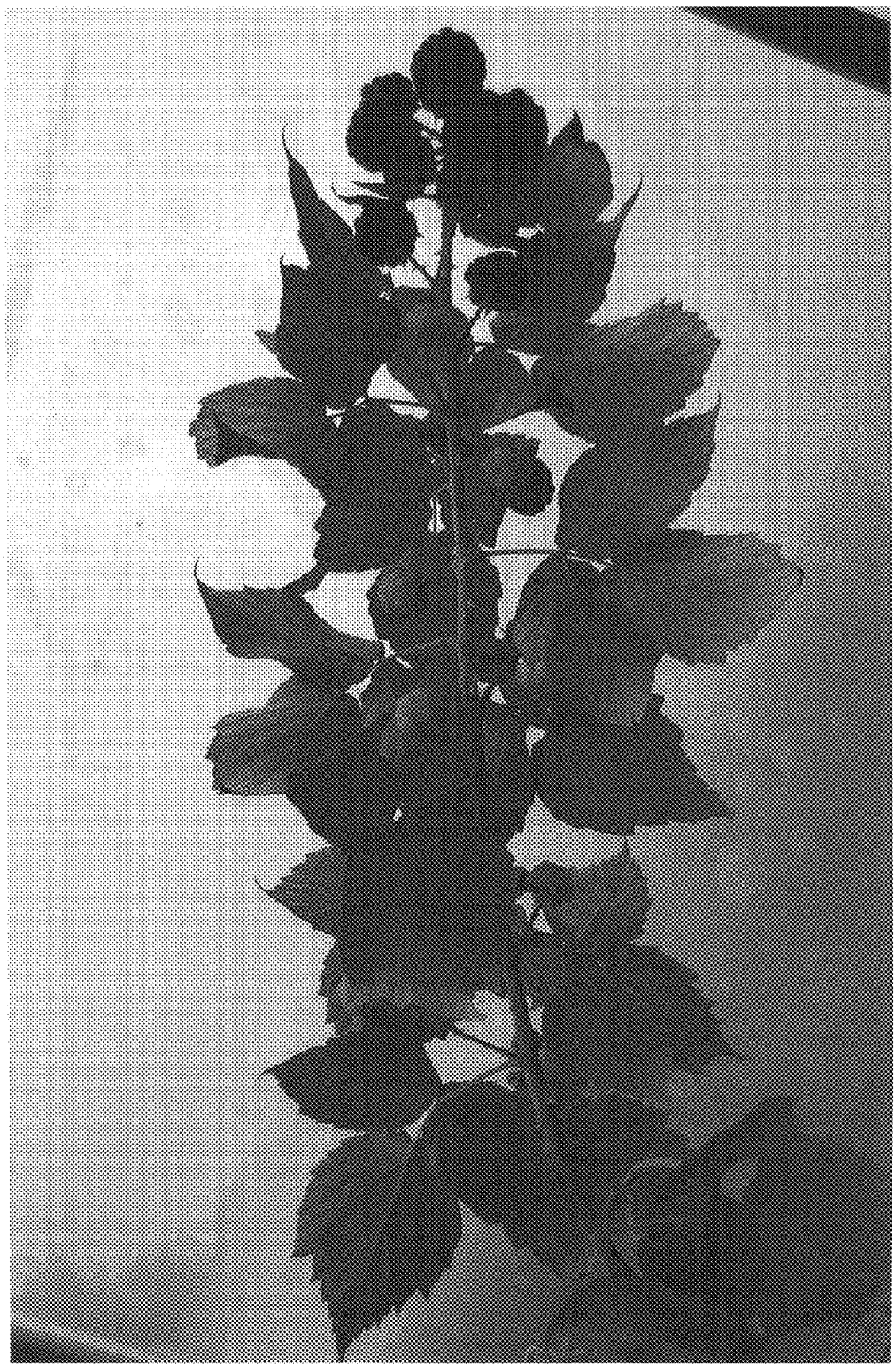
FIG. 3. shows the apical section of a primocane fruiting cluster of 'Ohio's Treasure', showing the exposure of 'Ohio's Treasure' fruit as grown in an unheated tunnel. The distance from the left to right margin of the illustration is 4 feet.

2. For basal floricane trusses, total node number averages 35, with 16.5 of the nodes bearing flowers and fruit, truss length averages 92.7 cm. (FIG. 1). Number of thorns per node average 3.5 or 42 per 30 cm of cane. Long basal floricane trusses average 4 short branches which can be considered as part of the floral truss. On average 52.8 fruit are produced per basal floricane truss.
3. For an unpruned primocane that is terminated by a flower cluster, on average, total node number per cane is 46, with 33 of the basal nodes staying vegetative and the top 13 nodes bearing flowers and fruit (FIG. 3). Total length of fruiting primocane canes averages 141 cm. Number of thorns per node are 1.5 or 14.5 spines per 30 cm of cane. Unpruned and floral canes also produce 5 branches. On average, 86.5 fruit are produced per unpruned primocane.
4. For pruned (apex removed) primocane laterals terminated by flowers, fruit is borne on lateral branches which arise from axillary buds. The total node number per lateral is, on average, 26, with 7.5 nodes producing flowers and fruit. Primocane lateral length averages 41 cm. Number of thorns per node average 3.3 or 63 thorns per 30 cm of cane. Primocane lateral branches average 0.8 secondary lateral branches. On average, each lateral produces 22.7 fruit.

For all buds not used in the first year of primocane growth for production of fruit, typical black raspberry floricane trusses form. These trusses average 36.6 cm in length and 15.1 nodes, of which, the most apical 4.3 nodes on average produce fruit. Fruit per truss averages 9.4.

Main cane diameter at the 30 cm height averages 1.0 cm. Canes are generally semi erect. Cane coloration on all canes during the growing season is light greyed-green, reminiscent of RHS Colour Plate No 191C. Canes develop their normal woody color in the fall changing from green to the red blush color (RHS Colour Plate No. 61A) then to dark purple (RHS Colour Plate No. N77A). Finally, canes develop a dark violet blue (RHS Colour Plate No. N186C or 187A) at their typical cane death after flowering.

Thorn shape is typical of black raspberry, stout, with a winged base narrowing apically to a thin needle which is slightly basal pointing (FIGS. 1 and 3). A full sized thorn length is approximately 3 mm. 'Ohio's Treasure' thorn color is similar to the cane greyed-green color during the early growing season (RHS Colour Plate No. 191C). By the last months of the growing season, base of the thorn darkens to red, then violet red (RHS Colour Plate Nos. N77A and N77B). The tip of the thorn becomes brown (RHS Colour Plate No. 177C). A similar pattern occurs with lateral buds, which turn green to red violet (RHS Colour Plate Nos. 77A and 77B) and are typical in size and shape of the species. No secondary buds were observed on 'Ohio's Treasure'.

The lower surface of all 'Ohio's Treasure' leaves is pubescent grey-green resembling RHS Colour Plate No. 191B and 191C. The upper surfaces of both primocane leaves are medium green, most closely in hue to RHS Colour Plate No. 137A and 137B, depending on the amount of N fertilization and time of season. Senescing leaves have a green yellow color resembling RHS Colour Plate No. 146A. Fall coloration includes red interveinal areas (RHS Colour Plate No. 61A). Leaves abscise readily in October and November. Petioles, petiolules and major veins are waxy and similar in color to the undersurface of the leaves, RHS Colour Plate No. 191C.

Vigorous plants have leaves that are greater than 98% trifoliolate, with only an occasional monofoliolate leaf in the apex of a fruiting cluster, among the fruit. The trifoliolate terminal leaflet is, on average, 4.7 cm. wide and 8.1 cm. long on floricane trusses and 6.2 cm wide and 9 cm. long on primocane trusses. The trifoliolate maximum leaf width, measured from apex of the lateral leaflet to the opposite lateral leaflet apex is, on average, 12.9 cm. on floricane trusses and 15.0 cm on primocanes. The width of the basal lateral leaflet for trifoliolate floricane truss and primocane leaves averaged 3.4 cm and 4.1 cm., respectively. Leaf size is smaller at the cane tips in fruiting clusters and on rat tails where the length of a monofoliolate leaf averages 5.8 cm in length and 1.8 cm in width.

The trifoliolate leaf petiole and petiolule lengths averaged 2.6 cm. and 1.1 cm. respectively on floricanes and 3.7 cm. and 1.8 cm on larger primocane leaves. Petioles, petiolules and leaf veins have a similar color to the midseason primocane (RHS Colour Plate No. 191C). Petioles have between 2 and 4 reduced size thorns, with 1 or 2 very reduced sized, more needle-like thorns occurring on the leaf midrib. Lateral leaflets are sessile and join at the petiole apex with the apical leaf petiolule. Leaf serration is relatively simple sawtooth with uneven "teeth" size. Leaves have moderate laminar puckering and venation pattern are common for most cultivars of black raspberry and cannot be used to distinguish this cultivar. Leaf veins are moderately pronounced on the undersurface of the leaf, with less than 20% of the circumference buried in the leaf lamina. Leaf stipules are bladelike, less than a mm in width, and 0.4 cm in length on floricane leaves but 0.8 cm long on larger primocane leaves.

The unscented flower morphology and early fruit morphology is typical of most black raspberry cultivars, having five white (RHS Colour Plate No. 155D) petals that average 0.7 to 0.9 cm. long, 0.3 to 0.4 cm. wide; petals abscise after pollination. The receptacle averages 0.7 cm in diameter, producing a flower diameter when flattened, approximately 2 cm in diameter on larger early flowers and 1.5 cm on secondary or tertiary truss position flowers. Basal floricane long trusses occasionally have flowers with 6 to 9 petals. Flowers have five 0.7 to 0.9 cm. long, 0.3 to 0.4 cm. wide at the base triangular grey green sepals (RHS Colour Plate No. 191C) on green peduncles (RHS Colour Plate No. 194B) which are less waxy than the rest of the cane and its attachments (FIG. 1). The internal sepal surfaces have two very thin stripes of pubescence running along their outside length.

Figure 4:
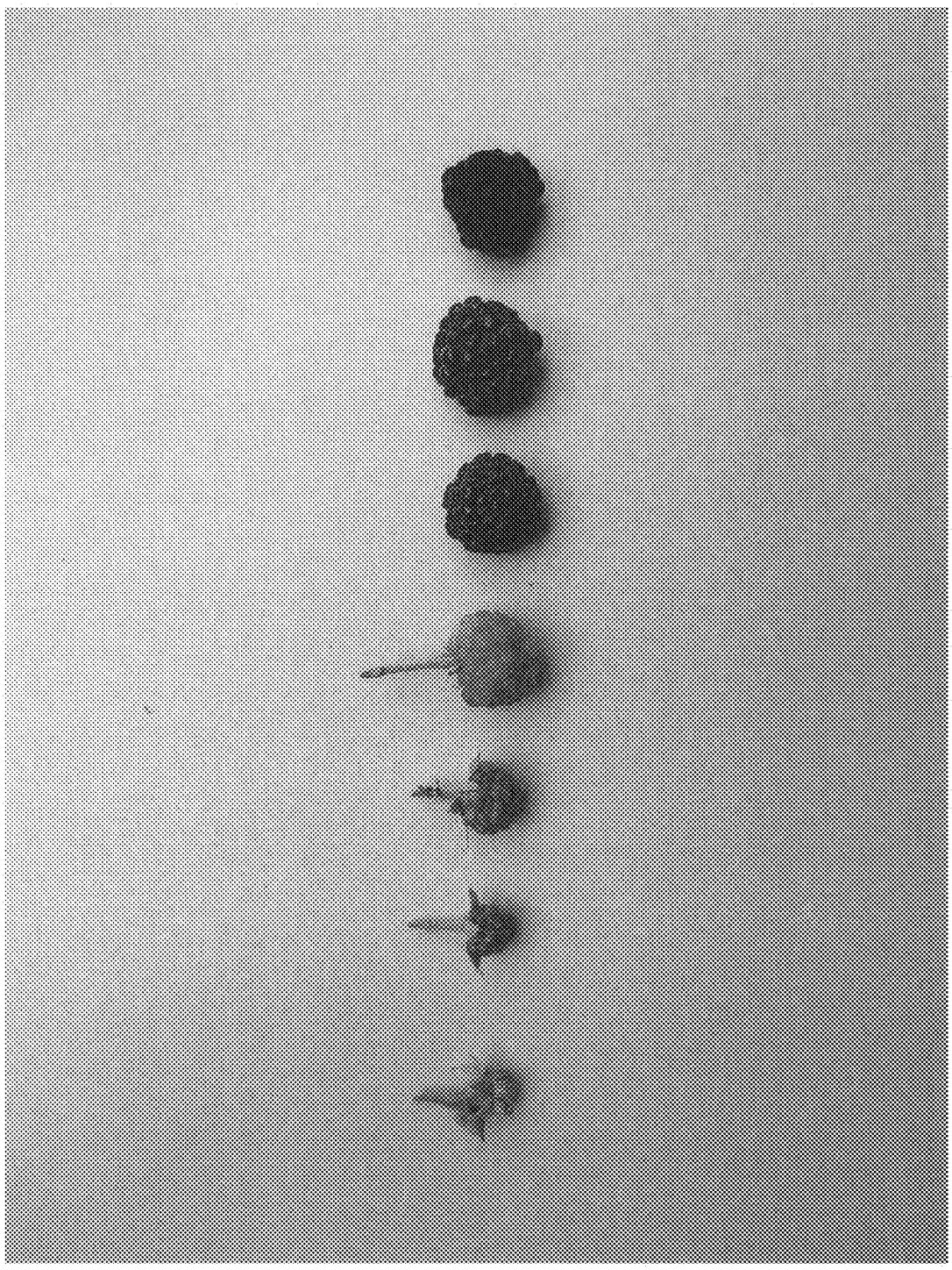
FIG. 4. shows the progression of 'Ohio's Treasure' fruit ripening from flowering to overripe (far right). The colors of the fruit when compared to the R.H.S. Colour Plates are: the green color fruit in the second and third fruit from the left (145B) the partially red fruit (44A), the black purple fruit third from the right (186A and 186B) and the glossy black (ripe) and dull black (over ripe) fruit (202A) on the right.

Mid season floricane flowers have on average 43 pistils on midseason fruit and a similar number of anthers, 38.4; primocane flowers have 57.4 pistils and 34.5 anthers. Both anthers and pistils seem to be functional at fertilization; cheese cloth covered flowers on screenhouse grown plants set seed. Anther, anther filament and pistil color is similar to RHS Colour Plate Nos. 160C, 160D and 144D, respectively; none of these traits can be used to identify 'Ohio's Treasure' (FIG. 4, left). Peduncle length is 1.5 cm. with an average of 21.1 thorns per peduncle.

Floricane flower trusses are typical determinate umbiliform cyme clusters, with most fruit clustered at the truss apex; typically 4 of the nodes produce flowers. Primocane flower trusses are more racimiform, with fruiting extending 13 nodes down the main cane and sometimes borne on short laterals with reduced leaves (FIG. 3). A typical (unpruned) primocane fruited cluster had the following number of fruit per node starting at the apex: 5, 2, 3, 3, 2, 3, 3, 2, 3, 4, 3, 6, 5, 5, 3, 1 followed by barren buds to the base of the cane, which are capable of fruiting after winter chilling. For each node which produces a branch with leafs, or branched peduncle with reduced leaves, the apical flower ripens first, as occurs in determinate cyme flower structures.

FRUIT PRODUCTION

As a result of the 4 types of fruiting patterns possible with 'Ohio's Treasure', the length of harvest season can be extended to 91 days of harvest over 105 calendar days. In overwintered pots in tunnels in western Maryland (2900 ft elevation), floricane trusses from chilled buds begin to ripen on June 27$^{th}$, are midseason (50% harvest) on July 8$^{th}$ and stop fruiting on July 14$^{th}$. Fruit weight averages 1.7 grams and overall yield is 437 grams per plant. Basal floricane long trusses commence harvest on July 16$^{th}$, are midseason on July 26$^{th}$ and stop fruiting on August 1$^{st}$. Fruit weight averages 1.9 grams and overall yield is 184 grams per plant. Primocane fruiting starts on unpruned canes and ends on pruned (summer topped) canes. The first unpruned cane harvest starts on August 16$^{th}$, is midseason on August 21$^{st}$ and stops fruiting on September 5$^{th}$; fruit weight averaged 1.8 grams (FIG. 7). Cut or summer topped primocanes start fruiting on September 12$^{th}$, are midseason on September 20$^{th}$ and stop fruiting on October 11$^{th}$; fruit weight averaged 2.1 grams. October harvest is not particularly large in western Maryland as frost is common in late September. Unripe fruit was wasted, however no attempt was made at measuring cold damaged, unripe, fruit. Over the year, total per plant yield was 930.3 grams and average fruit weight (total weight of harvest/total number of fruit) over the whole season was 1.9 grams.

Figure 6:
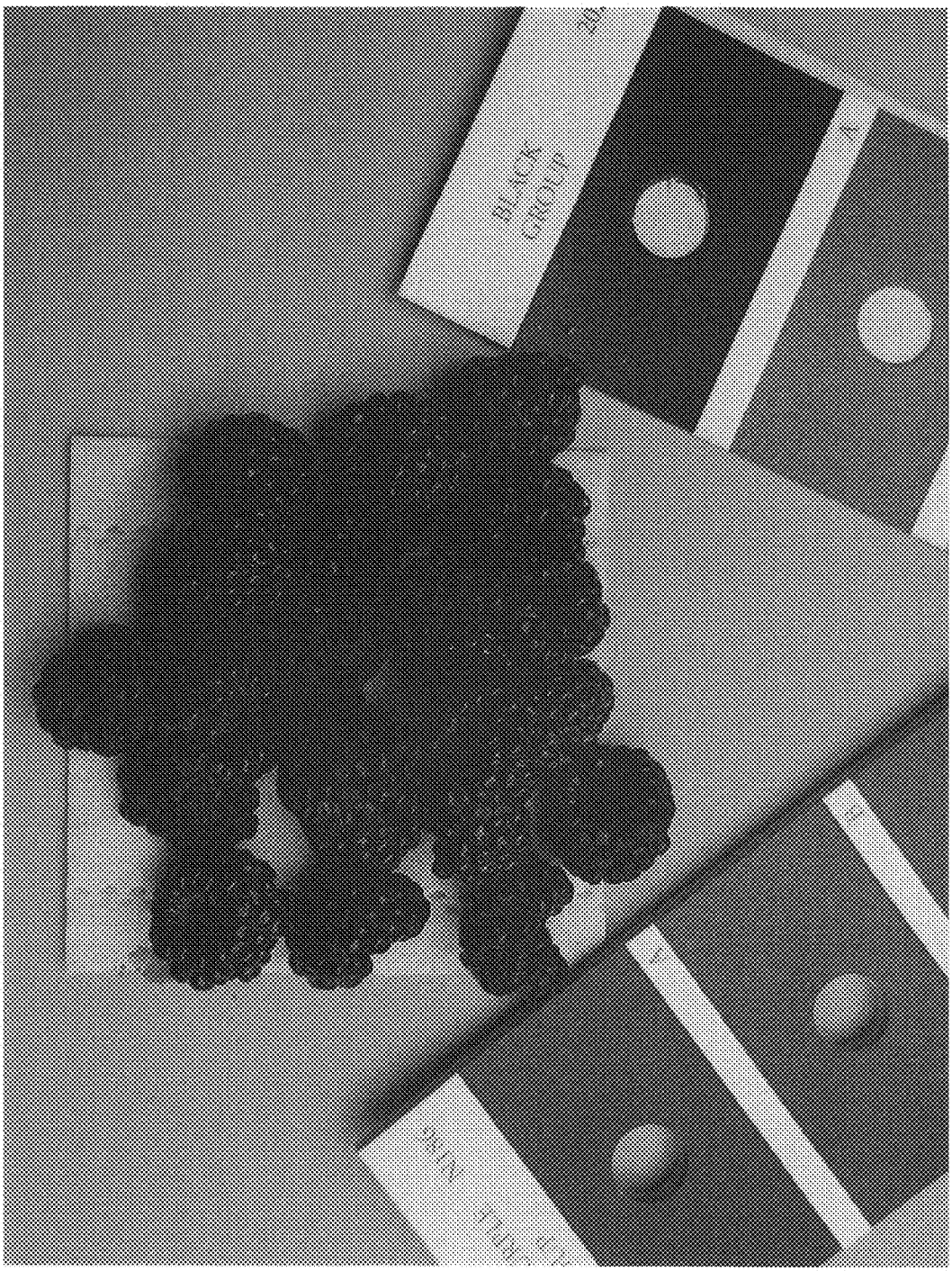
FIG. 6. shows the purple black color of unripe, but harvestable 'Ohio's Treasure' fruit and RHS. Colour Plate No. N186A and B, and the black ripe fruit near RHS Colour Plate No. 202.

The season gap between the end of the floricane and basal floricane crop and the beginning of this primocane crop is 14 days, compared to 39 days for the early red raspberry spring and fall fruiting cultivar 'Jaclyn' (U.S. Plant Pat. No. 15,647) 'Ohio's Treasure' fruit size and weight are moderate, but relatively consistent through the season, perhaps larger in the fall because of the cooler temperatures or natural anatomy and behavior of the different fruiting structures. For average fruit of 1.9 grams, fruit length (base to apex) is 1.34 cm and fruit width is 1.83 cm., making the shape of 'Ohio's Treasure' fruit round and somewhat squat (FIG. 6). The receptacle cavity averages 0.83 cm. Thus, the fruit width to receptacle cavity is 45% of the fruit diameter, similar to the round fruited red raspberry, 'Josephine' (U.S. Plant Pat. No. 12,173, which has a cavity 40% of the fruit diameter. For this sample, average number of formed drupelets was 57.4 and average number of aborted (undeveloped) drupelets was 3.4 per fruit. Thus, drupelet set was 94%. The uneven appearance of 'Ohio's Treasure' is not evidently due to aborted drupelets. XEF-o1, a parent of 'Ohio's Treasure' exhibited a similar tendency toward uneven drupelet formation, therefore a genetic cause for this appearance is possible. Average drupelet weight was 33 mg, which was consistent over fruit from 1.0 to 2.6 grams in weight.

Figure 5:
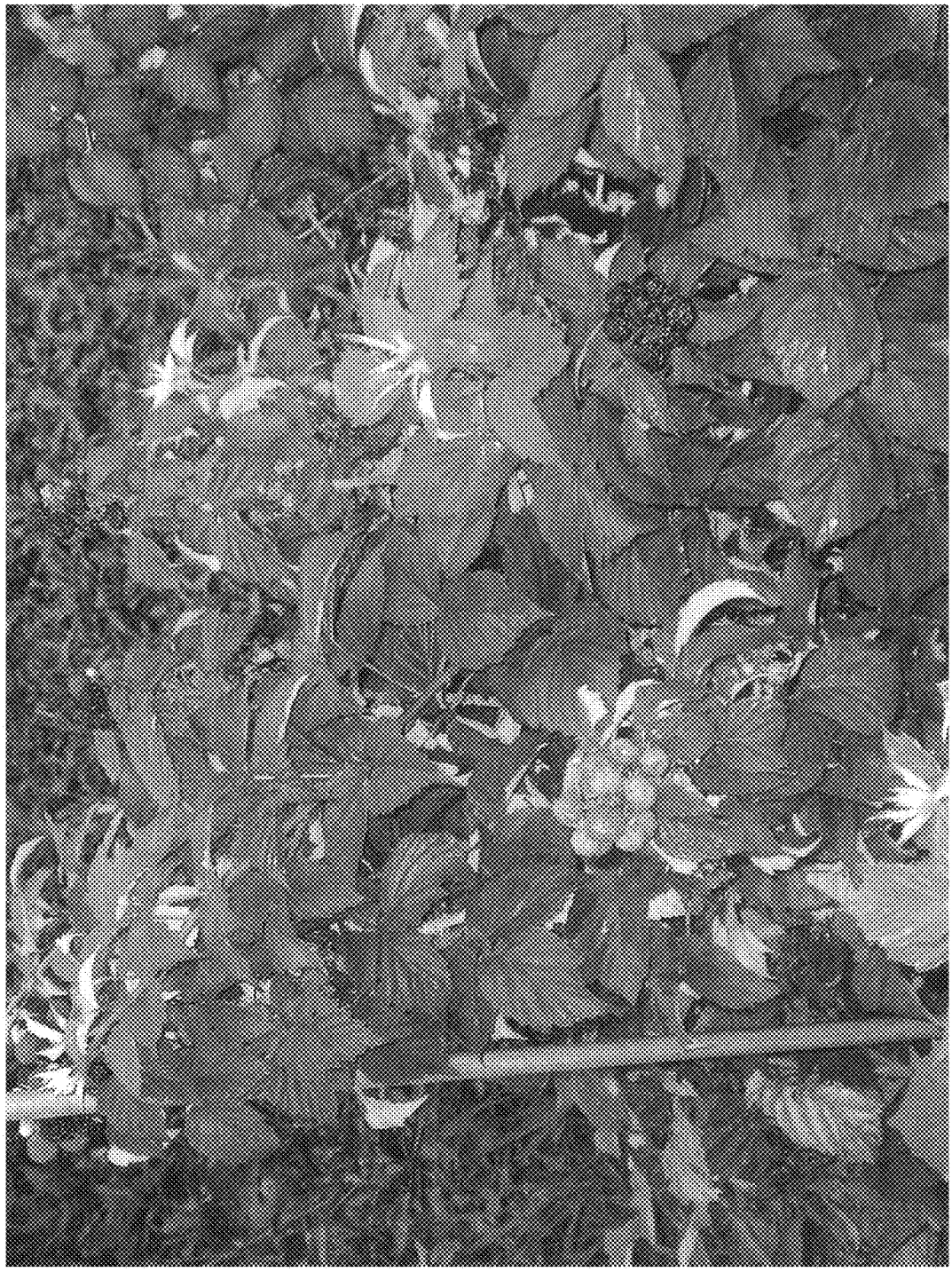
FIG. 5. shows a primocane fruiting 'Ohio's Treasure' plant in August as grown in a field in Wilmington, Ohio.

'Ohio's Treasure' fruit are black (RHS Colour Plate No. 202A) (FIGS. 4, 5 and 6), cohesive, and under normal circumstances, the fruit does not shatter under pressure of hand harvest. Except when temperatures fall into the 50°'s during the day, slightly unripe fruit is pickable when purple black (RHS Colour Plate No. 186A). The texture of the fruit is relatively softer than other commercially grown eastern US-grown black raspberry cultivars known to us, reminiscent of older black raspberry varieties. Ripe fruit progresses from glossy to dull at overripe, typical of the species (FIG. 4).

PEST AND DISEASE RESISTANCE

No reaction has been noted to black raspberry pests, as the test plants have been grown in tunnels, with lower disease and insect incidence. Field grown plants are free of orange rust, but an insufficient amount of time has passed to determine whether there is a practical resistance to this fungus from the immune red raspberry parents used. Fruit is usually free from *Botrytis* rot in the tunnel, but field grown plants, fruit rot can develop. Mildew infestation in the tunnel has not been substantial, requiring no sprays for control.

DIFFERENCE FROM OTHER BLACK RASPBERRY

The following characteristics are useful in distinguishing 'Ohio's Treasure' from other cultivars and can be useful for cultivar identification. Plants used for these observations were grown in uncrowded pots in clear plastic unshaded tunnels or greenhouses.

1. When cane density is below 9 canes per pot on plants at least two years old, 'Ohio's Treasure' plants produce fruit on unused overwintered buds on floricanes, either late fruiting long basal trusses or typical black raspberry trusses that arise from more apical buds. Unlike commercially available black raspberry cultivars, 'Ohio's Treasure' will also produce fruit later on primocanes which terminate in flower clusters either as a main cane and cane branches or as forced branches from summer pruned primocanes. This combination of fruiting sites results in harvest over 91 days, compared to less than a month for floricane fruiting cultivars.
2. For non-pruned primocanes, fruit appear on average at the 34$^{th}$ node from the base of the plant. If the main cane is topped, or the apex removed by pruning, the lateral branches grow, on average, 18 nodes before flowering. By comparison, 'Jaclyn' (U.S. Plant Pat. No. 15,647), 'Marcianna' (U.S. Plant Pat. No. 21,007), 'Caroline' (U.S. Plant Pat. No. 10,412) and 'Heritage' (unpatented) produce red raspberry fruit on primocanes, on average, at the 15$^{th}$, 24$^{th}$, 25$^{th}$ and 29$^{th}$ nodes, respectively. Although no data was presented on the location of the first node that produces fruit on 'Explorer' primocanes, fruiting 'Explorer' plants were reported to be shorter than 'Ohio's Treasure' plants although the observations were made in very different climates.
3. 'Ohio's Treasure' fruit is larger than 'Explorer' and similar or superior in weight to all other black raspberry cultivars except 'Jewel' (unpatented), 'Black Hawk' (unpatented) and 'Dundee' (unpatented).
4. Unlike all the other cultivars, larger 'Ohio's Treasure' fruit are not smooth, having an uneven appearance because of mismatched drupelet size. This lack of smoothness is probably genetic in nature; XEF-o1, a parent, has similar rough fruit. On average, less than 6% of 'Ohio's Treasure' drupelets abort and fail to develop; aborted drupelet because of poor seed set is a major reason for uneven or crumbly fruits in *Rubus*.

5. An identifying cane structure in *R. occidentalis* L. is the formation of "rat tail" growth in early fall which is used in propagation of black raspberries through "tip layering", the insertion of apex of a shoot into rooting medium or soil to stimulate the formation of a whole, rooted, plant. 'Ohio's Treasure' produces classic rat tail growth and these structures tip layer (root) readily. In *Rubus*, thorn color pattern and size vary by genotype, but are consistent over most environments and are typical of the variety or species. 'Ohio's Treasure' has thorn number and form typical of black raspberries on its canes throughout the growing season, the exception being a greater amount of more needle like thorns on rat tail growth. This intermediate thorn pattern and quantity is the most reminiscent character of 'Ohio's Thornless' to *R. idaeus* L. the red raspberry. Compared to 'Explorer', the only other fall bearing, moderately large sized, black raspberry, 'Ohio's Treasure' thorns are more numerous. Like 'Explorer', the number of thorns is greater in the fruit peducle.

6. Flowers on long, basal floricane flower trusses and primocane flower truss morphology is more racimiform than then the rest of the plant and other varieties and represents a key identifying feature of 'Ohio's Treasure'. Flowers on these structures can have more than 5 petals

What is claimed:

1. A new and distinct fall bearing black raspberry plant known as 'Ohio's Treasure' as described herein, illustrated and identified by the characteristics set forth above.

* * * * *